US 7,672,722 B1

(12) United States Patent
Mengotto

(10) Patent No.: US 7,672,722 B1
(45) Date of Patent: Mar. 2, 2010

(54) HARDWARE-BASED STATE MACHINE FOR USE IN DISCRIMINATING NEAR FIELD SIGNALS FROM FAR FIELD SIGNALS FOR USE IN AN IMPLANTABLE CARDIAC STIMULATION DEVICE

(75) Inventor: Curtis Mengotto, Sherman Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 1025 days.

(21) Appl. No.: 11/316,253

(22) Filed: Dec. 21, 2005

(51) Int. Cl.
*A61N 1/00* (2006.01)

(52) U.S. Cl. .................................................. 607/9

(58) Field of Classification Search ............ 607/4, 607/5, 9, 14, 17, 18, 28; 600/544, 508, 515
See application file for complete search history.

(56) References Cited

U.S. PATENT DOCUMENTS

| | | | | |
|---|---|---|---|---|
| 4,059,116 A * | 11/1977 | Adams | ............ | 607/9 |
| 6,366,810 B1 * | 4/2002 | Johnson et al. | ............ | 607/9 |
| 6,516,225 B1 * | 2/2003 | Florio | ............ | 607/9 |
| 6,522,921 B2 | 2/2003 | Stahmann et al. | ............ | 607/9 |
| 6,625,488 B2 * | 9/2003 | Poore et al. | ............ | 607/9 |
| 6,731,978 B2 * | 5/2004 | Olson et al. | ............ | 607/4 |
| 2002/0082650 A1 | 6/2002 | Stahmann et al. | ............ | 607/9 |
| 2006/0241697 A1 * | 10/2006 | Libbus et al. | ............ | 607/2 |
| 2007/0118042 A1 * | 5/2007 | Wang | ............ | 600/508 |
| 2007/0244408 A1 * | 10/2007 | Wingeier et al. | ............ | 600/544 |

FOREIGN PATENT DOCUMENTS

| EP | 1 123 716 A2 | 8/2001 |
|---|---|---|
| EP | 1 123 716 A3 | 8/2001 |

* cited by examiner

*Primary Examiner*—George Manuel
*Assistant Examiner*—Robert N Wieland

(57) ABSTRACT

A hardware-based state machine is provided for use in a pacemaker or other implantable cardiac stimulation device for use in discriminating near field signals sensed in the atria from far field signals emanating from the ventricles. The state machine is interposed between atrial/ventricular channel sense amplifiers and a main microcontroller of the device. The state machine operates to quarantine each P-wave interrupt received from the atrial channel sense amplifier to determine whether the P-wave interrupt corresponds to a true P-wave (i.e. a near field P-wave) as opposed to a false P-wave (i.e. a far field R-wave). Interrupts corresponding to true P-waves are forwarded by the quarantine circuit to the microcontroller after a short time delay. Interrupts corresponding to false P-waves are not forwarded. Hence, the microcontroller receives only true P-wave interrupts and therefore does not need to devote processing resources to distinguishing between true P-waves and false P-waves.

10 Claims, 8 Drawing Sheets

US 7,672,722 B1

HARDWARE-BASED STATE MACHINE FOR USE IN DISCRIMINATING NEAR FIELD SIGNALS FROM FAR FIELD SIGNALS FOR USE IN AN IMPLANTABLE CARDIAC STIMULATION DEVICE

FIELD OF THE INVENTION

The invention generally relates to implantable cardiac stimulation devices such as pacemakers and implantable cardioverter/defibrillators (ICDs) and, in particular, to techniques for discriminating near field signals sensed in the atria from far field signals emanating from the ventricles.

BACKGROUND OF THE INVENTION

Many pacemakers and ICDs include one or more leads mounted in the atria for directly sensing atrial events, particularly P-waves. Reliable P-wave detection is required so as to determine the atrial rate for detecting atrial fibrillation and for controlling atrial pacing functions, such as dynamic atrial overdrive (DAO) pacing. A long-standing problem with atrial sensing is that electrical signals generated in the ventricles (R-waves) often appear within the signals sensed within the atria and can be misinterpreted as P-waves. Electrical signals that originate in a different chamber of the heart from where the signals are sensed are referred to as far field signals. Electrical signals that originate in the chamber of the heart in which they are sensed are referred to as near field signals. Hence, the general goal is to discriminate near field signals from far field signals.

Since the ventricles are considerably more massive than the atria, depolarization of ventricles generates R-waves having magnitudes far greater than P-waves. Even when sensed with leads mounted within the atria, the far field R-waves often appear with at least the same magnitude as the near field P-waves, making it quite difficult to reliably detect only P-waves. Note that, strictly speaking, P-waves and R-waves are features of a surface electrocardiogram (EKG). Herein, the terms P-wave and R-wave are also used to refer to the corresponding internal electrical signal component, i.e. the corresponding component of an intracardiac electrogram (IEGM).

In dual chamber modes, far field R-wave sensing is normally thought of as an R-wave followed by a P-wave. A sufficiently long Post-Ventricular Atrial Refractory Period (PVARP) is used to prevent far field sensing when the sensing order is R-P, i.e. the R-wave is sensed before the P-wave. However, a second case of far field sensing exists in which the far field R-wave is sensed in the atrial channel before the associated R-wave is sensed in the ventricular channel. Traditional PVARP is not helpful in this case since the far field R-wave appears on the atrial channel signal before the PVARP begins.

The second type of far field sensing (i.e. the P-R type) is illustrated in FIG. 1, which shows atrial and ventricular sense amplifier signals 2 and 4, respectively, along with a corresponding surface EKG cardiac signal 6. As can be seen, an R-wave 7 appears as a far field signal in the atrial sense amplifier signals (though reversed in polarity in this particular example.) Far field sensing of the P-R type is often caused by the relationship between the atrial and ventricular sensing thresholds with respect to the sense waveforms. P-R type far field sensing is also dependent to lead positioning, as well as on the frequency response of any band-pass filters provided on the sensing channel. In particular, a narrow band-pass filter can cause ringing and peak detections away from the actual signal. Such filters are employed to limit sensed events to only P/R wave morphologies.

FIG. 2 shows a detailed example of far field R-wave sensing. Both atrial and ventricular channel signals 8 and 9, respectively, respond to a physiological ventricular depolarization. However, because of ringing and sensing threshold settings, the atrial channel 8 senses the far field R-wave before the R-wave is sensed in ventricular channel 9. In particular, the atrial channel senses the R-wave when its signal magnitude exceeds the atrial channel sensing threshold, which occurs before the ventricular channel senses the R-wave (when its signal magnitude eventually exceeds the ventricular channel sensing threshold.) The far field R-wave that is sensed on an atrial channel signal is misinterpreted as a P-wave and thereby resets timing intervals. A device with no protection against far field sensing of the P-R type (1) may be susceptible to large number of Auto Mode Switches (AMS), (2) may be less capable of detecting and responding to atrial arrhythmias, (3) may exhibit high inappropriate atrial rate Stored Electrograms, and (4) may record skewed diagnostics. In particular, the device may count both the true P-wave and the far field R-wave on the atrial channel for the purposes of atrial rate calculation, likely resulting in the calculated atrial rate being twice the actual atrial rate. For ICDs configured to deliver a high energy cardioversion shock to terminate atrial fibrillation, the erroneous calculation of the atrial rate may result in a painful cardioversion shock being delivered even though none is required.

P-R type far field sensing problems were addressed in U.S. Pat. No. 6,516,225 to Florio, entitled "System and Method for Distinguishing Electrical Events Originating in the Atria from Far field Electrical Events Originating in the Ventricles as Detected by an Implantable Medical Device." Using techniques described therein, far field R-waves in the atria are distinguished from true P-waves using both a post ventricular atrial blanking (PVAB) interval and a separate pre-ventricular blanking interval (pre-VAB) interval. Upon detection of a P-wave in an atrial channel signal, the device begins tracking a pre-VAB interval. If an R-wave is then detected in a ventricular channel signal during the pre-VAB interval, the P-wave is rejected as being a far field R-wave. A PVAB interval may also be employed to filter out any P-waves detected in the atria immediately following detection of an R-wave in the ventricles. In another example, far field R-waves are distinguished from true P-waves using template matching. P-waves detected in the atria are compared against a template representative of true P-waves. If the P-wave substantially matches the template, the P-wave is deemed to be a true P-wave; otherwise the P-wave is rejected as being a far field R-wave or other anomalous electrical event.

Although the technique of Florio is effective, room for improvement remains. In particular, the technique of Florio is primarily a microprocessor-based technique, i.e. the algorithms performed to discriminate far field and near field atrial signals are implemented in software using a microprocessor. Although the techniques successfully detect and reject far field R-waves from the atrial channel, the techniques are relatively costly in terms of software complexity and microprocessor duty cycle time. With ever greater burdens placed on device microprocessors to detect and respond to a wide range of arrhythmias or other medical conditions, it would be desirable to instead provide hardware-based techniques for discriminating far field and near field atrial signals.

One hardware-based technique is described in U.S. patent application Ser. No. 10/430,039 of Kroll et al., filed May 3, 2003, entitled "System and Method for Rejecting Far field Signals using an Implantable Cardiac Stimulation Device." A Boolean logic circuit is described therein for filtering far field electrical cardiac signals from near field signals wherein atrial tip and ring signals are sensed using unipolar electrodes. Any timing differences between corresponding events within the signals are detected. Then, far field signals are filtered from the tip and ring signals based on the detected timing differences, such that substantially only near field atrial signals remain. The circuit exploits the fact that near field atrial signals are sensed when a conduction wave passes by the atrial electrodes. In contrast, far field signals from the ventricles propagate to the atrium at near the speed of light. Hence, any significant timing difference between corresponding events appearing in the atrial signals is indicative of a near field event, whereas the lack of a significant timing difference is indicative of a far field event.

It would be desirable to provide alternative hardware-based techniques for discriminating far field and near field atrial signals.

SUMMARY

In accordance with one embodiment, a system is provided for use in an implantable cardiac stimulation device. The system includes sensing circuitry operative to sense electrical cardiac signals indicative of possible cardiac depolarization events and to generate event interrupts in response thereto, and a microcontroller operative to control cardiac stimulation therapy in response to the interrupts. The system also includes a quarantine circuit, interposed between the sensing circuitry and the microcontroller, and operative to quarantine selected event interrupts.

In one example, the quarantine circuit operates to quarantine each atrial depolarization event interrupt, i.e. each P-wave interrupt, for a predetermined period of time, such as 16 milliseconds (ms). During that time, the quarantine circuit determines whether the P-wave interrupt corresponds to a true P-wave rather than a far field R-wave (i.e. a false P-wave). Interrupts corresponding to true P-waves are forward by the quarantine circuit to the microcontroller after the period of time elapsed. Interrupts corresponding to false P-waves are not forwarded to the microcontroller at all. Hence, the microcontroller receives only true P-wave interrupts on the atrial channel and therefore does not need to devote processing resources to distinguishing between true P-waves and false P-waves (i.e. far field R-waves) In other words, the discrimination of true P-waves from false P-waves is performed entirely using hardware so that microcontroller processing resources can be devoted to other tasks.

Note that, with this implementation, P-wave interrupts are delayed, but R-wave interrupts are not. Preferably, the microcontroller is configured to take the P-wave interrupt delay into account when calculating P-R intervals or when timing the delivery of therapy to the atria. For example, if P-wave interrupts are subject to a 16 ms delay, the microcontroller (or other internal or external component) automatically adds 16 ms to the calculated P-R, P-A and V-P intervals so as to recover the true intervals.

In a preferred implementation, the quarantine circuit is implemented as a hardware state machine in conjunction with a hardware timer. The hardware state machine operates, in response to receipt of an atrial depolarization event interrupt, to forward a validated (or "true") atrial event interrupt to the microcontroller after the timer expires, so long as no ventricular depolarization event interrupt is also received before the timer expires. In one specific example, the state machine is operative to selectively transition among an "idle state," a "quarantine state," a "true atrial depolarization event state (i.e. a true P-wave state)," and a "false atrial depolarization event state (i.e. a false P-wave state)." Receipt of an atrial event interrupt while in the idle state, without receipt of a substantially simultaneous ventricular depolarization event interrupt, triggers a transition from the idle state to the quarantine state. Expiration of the timer while in the quarantine state, without receipt of a ventricular depolarization event interrupt prior to expiration of the timer, triggers a transition to the true atrial depolarization event state. Transition to the true atrial depolarization event state triggers output of the atrial depolarization event interrupt to the microcontroller. Alternatively, receipt of a ventricular depolarization event interrupt while in the quarantine state triggers a transition to the false atrial depolarization event state. Expiration of the timer while in the false atrial depolarization event state triggers a transition to the idle state. Additionally, the substantially simultaneous receipt of both an atrial event interrupt and a ventricular event interrupt while in the idle state triggers a transition to the false atrial depolarization event state, followed eventually by a transition back to the idle state once the timer expires. The state machine may be implemented, e.g., as a Moore-type circuit with D-flip flops, with the timer implemented as a pre-loadable counter/register.

The period of time used to quarantine each P-wave interrupt is preferably a programmable parameter, which is set based on ringing characteristics of any bandpass filters used, as well as characteristics of the sense amplifiers themselves and characteristics of the leads and their placement.

Thus, an improved system is provided for discriminating true P-waves from false P-waves, i.e. far field R-waves, using hardware so that microprocessor resources are conserved. Other features, objects and advantages of the invention are set forth below. Method implementations of the invention are also set forth.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
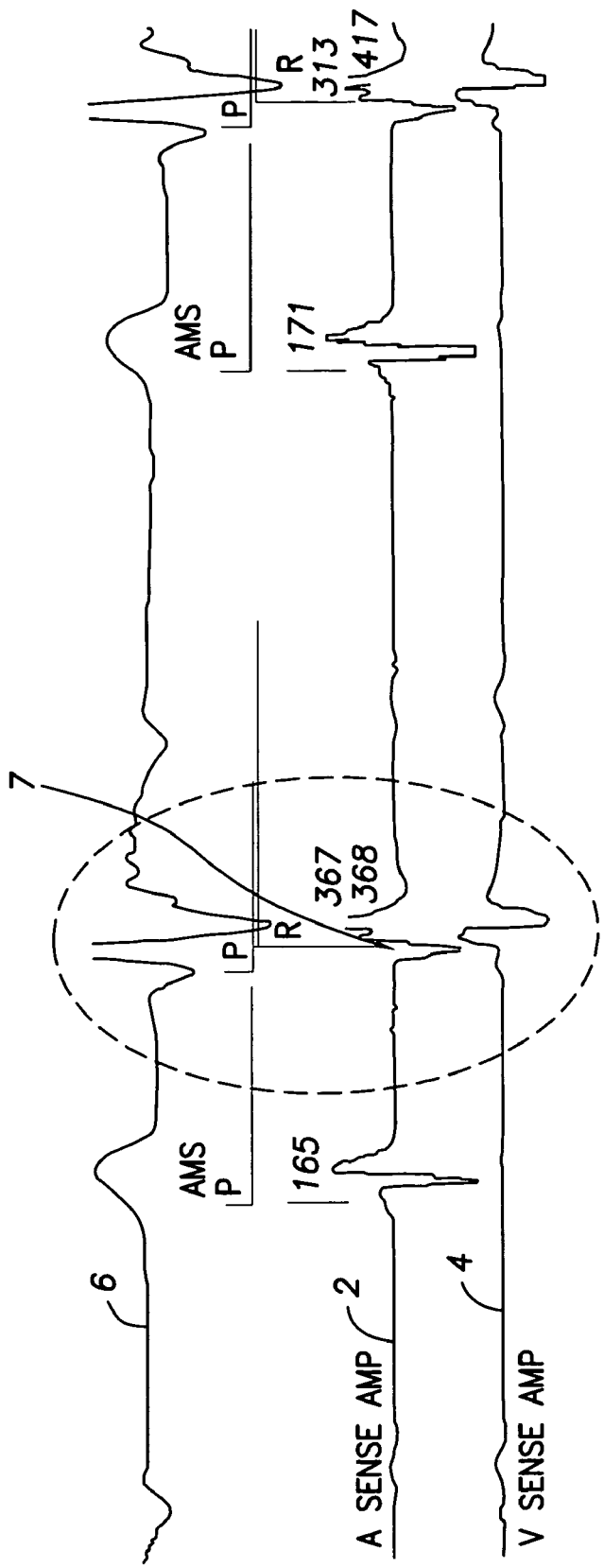
FIG. 1 is a graph illustrating P-R type far field sensing problems that arise in connection with prior art devices.
Figure 2:
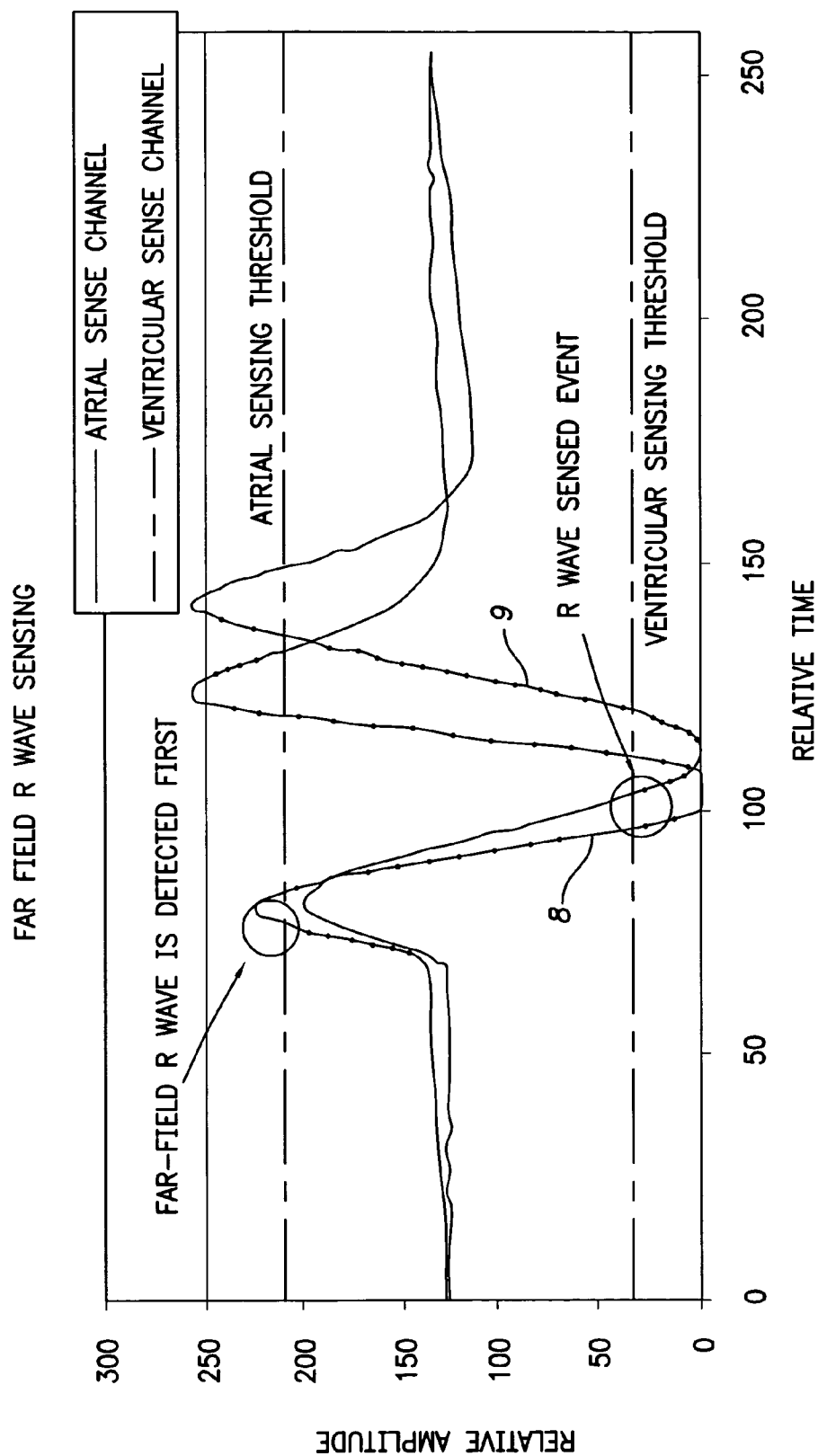
FIG. 2 is a graph further illustrating P-R type far field sensing problems that arise in connection with prior art devices, and particularly illustrating atrial and ventricular channel sensing thresholds that affect sensing times.
Figure 3:
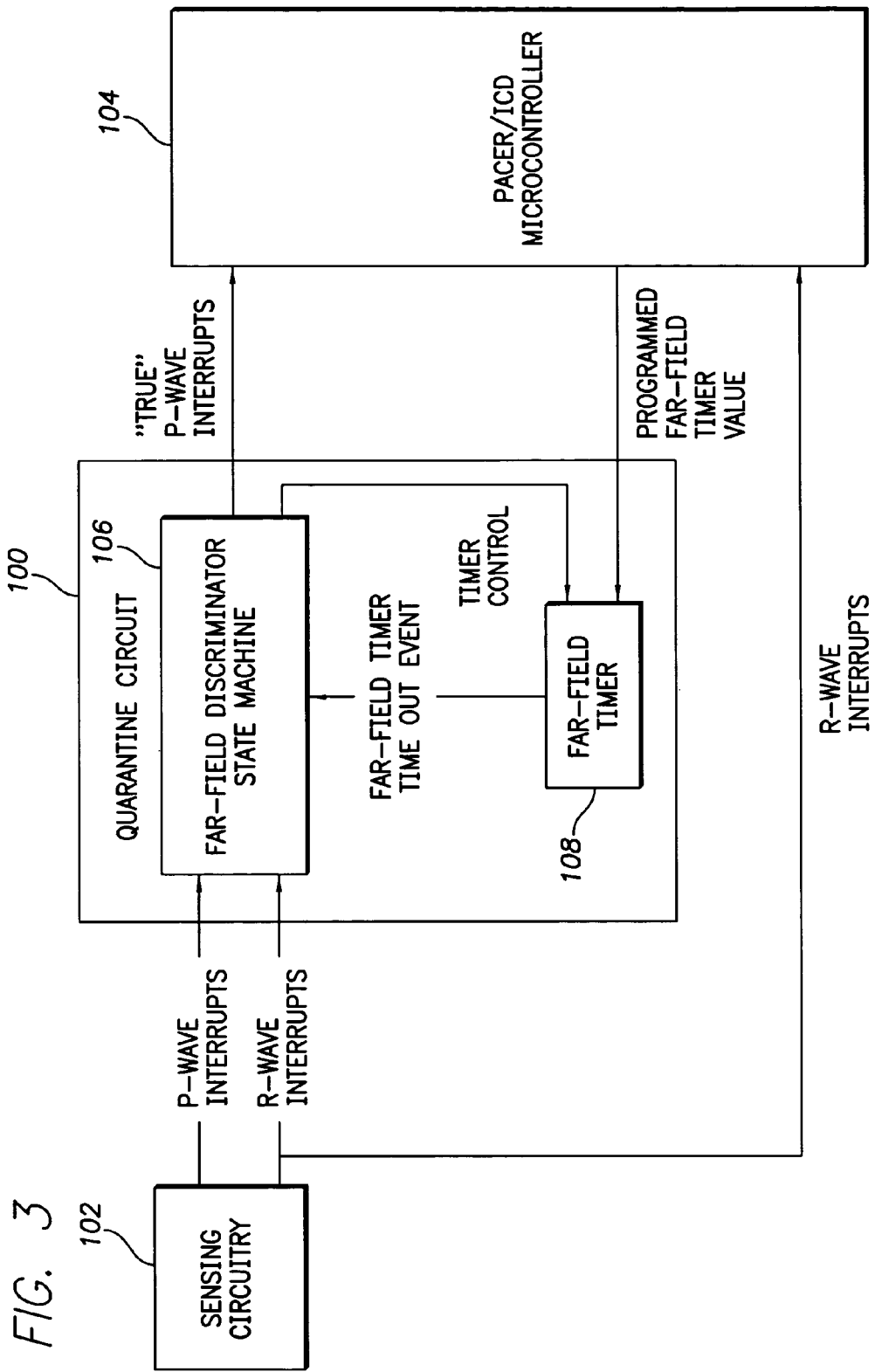
FIG. 3 is a block diagram illustrating a state machine-based quarantine circuit, configured in accordance with an exemplary embodiment of the invention, for quarantining P-wave interrupts.

FIG. 3 illustrates a quarantine circuit 100 for use with a pacer/ICD or other implantable cardiac stimulation device (such as the one illustrated in FIGS. 8 and 9, described below). Quarantine circuit 100 is interposed between sensing circuitry 102 (such as the atrial and ventricular sense amplifiers of the pacer/ICD), and software logic of a microcontroller 104 of the pacer/ICD. Sensing circuitry 102 is operative to sensed electrical cardiac signals indicative of possible cardiac depolarization events within the heart of the patient in which the pacer/ICD is implanted. The sensing circuitry is also operative to generate event interrupts in response to the depolarization events. In particular, the sensing circuitry generates P-wave interrupts in response to depolarization events sensed within the atria and generates R-wave interrupts in response to depolarization events sensed within the ventricles. Quarantine circuit 100 receives both the P-wave and R-wave interrupts and quarantines the P-wave interrupts until a determination can be made by the quarantine circuit as to whether the P-wave interrupt corresponds to a true P-wave (i.e. a near field P-wave) or a false P-wave (i.e. a far field R-wave). P-wave interrupts corresponding to true P-waves are forwarded to the microcontroller for further processing. P-wave interrupts corresponding to false P-wave are not forwarded to the microcontroller. In this manner, the software logic of the microcontroller receives only P-wave interrupts corresponding to true P-waves and therefore need not devote processing resources to distinguishing between true and false P-waves.

In one example, quarantine circuit 100 includes an automatic far field discriminator state machine 106 and a far field timer 108. State machine 106 receives both P-wave and R-wave interrupts from sensing circuitry 102. Upon receipt of a P-wave interrupt, state machine 106 forwards a timer control signal to timer 108, which begins timing a predetermined far field timer value received from microcontroller 104 set, for example, to 16 ms. When the timer interval elapses, timer 104 forwards a far field timer timeout event signal to state machine 106. If an R-wave interrupt is received by state machine 106 before the timeout signal is received (and this includes R-wave interrupts received substantially contemporaneously with the P-wave interrupt), the P-wave interrupt is deemed to correspond to a false P-wave and is not forwarded to the microcontroller. If, however, no R-wave interrupt is received prior to the timer elapsing, then the state machine forwards the P-wave interrupt to the software logic of the microcontroller. The microcontroller can then rely on the P-wave interrupt as being representative of a true P-wave and need not devote processing resources for distinguishing true P-waves from false P-waves.

The timer value is a programmable value set based on the characteristics of the sense amplifiers, any bandpass filters used (not separately shown), and other factors, such as the particular location of electrodes in the heart. Preferably, a default value (such as 16 ms) is programmed into the device following manufacture, based on the characteristics of the sense amplifiers and the bandpass filters. Then, following device implant, the physician may adjust the timer value, if needed, based on the particular leads used and their placement within the heart. In general, the programmable delay values are in the range of 0 to 60 ms, with 16 ms merely being one example.

Hence, interrupts corresponding to true P-waves are forwarded to the microcontroller, but each is subject to the time delay of the far field timer value. Interrupts corresponding to false P-waves are not forwarded to the microcontroller at all. Interrupts corresponding to R-waves are routed directly to the microcontroller, i.e. R-wave interrupts are not subject to any delay. The microcontroller responds to the P-wave interrupts and the R-wave interrupts, along with other input information, to control cardiac stimulation therapy delivered to the patient, such as delivery of pacing pulses to the atria and/or ventricles.

Since P-wave interrupts are delayed, but R-wave interrupts are not delayed, the microcontroller is preferably configured to take the P-wave interrupt delay into account when calculating P-R intervals or when timing the delivery of electrical stimulation therapy to the atria, such as atrial pacing pulses. In the example where the P-wave interrupts are subject to a 16 ms delay, the microcontroller automatically adds 16 ms to the calculated P-R interval to recover the true P-R interval. Alternatively, R-wave interrupts may be delayed by an equal amount of time so that the P-R interval calculated by the microcontroller is correct. However, since it is generally desirable for the microcontroller to be capable of responding promptly to R-waves, it is preferable for microcontroller to receive the R-wave interrupts substantially in real time, i.e. not subject to any delay. In this regard, defibrillation shocks are preferably synchronized with R-waves and such synchronization can be more readily and reliably achieved if R-wave interrupts are not delayed. Furthermore, it is not necessary to delay R-wave interrupts because far-field R-waves are uncommon due to the typically low signal strength of the atrial depolarization.

Figures 4, 5:
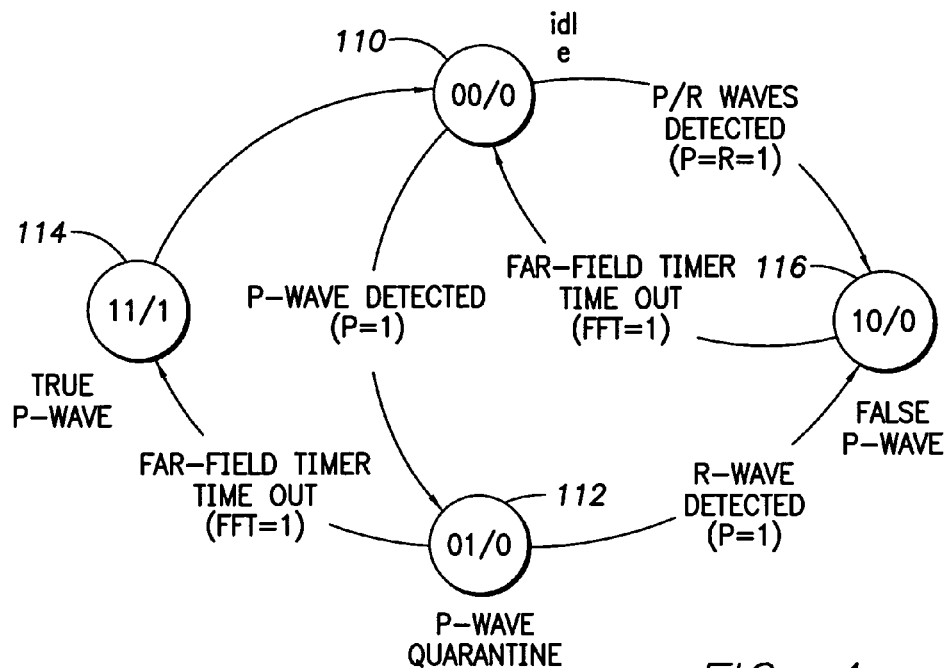
FIG. 4 is a state machine diagram illustrating states of the quarantine circuit of FIG. 3.
FIG. 5 illustrates truth tables for the state machine of FIG. 4.

Turning now to FIG. 4, a graphical representation of various states tracked by state machine 106 of FIG. 3 will now described. Initially, the state machine begins in an "idle" state 110, also denoted the "00/0" state. The state machine remains in the idle state until a P-wave interrupt is received from the sensing circuitry. Once a P-wave interrupt is received (assuming that an R-wave interrupt is not simultaneously received), the state machine transitions from the idle state to a P-wave quarantine state 112, also denoted herein as the "01/0" state. Receipt of the P-wave interrupt also triggers activation of the far field timer of FIG. 3. The state machine then remains in the P-wave quarantine state until either (1) the timer elapses or (2) an R-wave interrupt is received, whichever comes first. If the timer elapses before an R-wave interrupt is received, the state machine transitions from the P-wave quarantine state to a true P-wave state, i.e. a state wherein receipt of a non-far field P-wave is confirmed. The true P-wave state is also denoted herein as the "11/1" state or the "true atrial depolarization event state." Entry into the true P-wave state causes the P-wave interrupt to be forwarded to the microcontroller.

If, however, an R-wave interrupt is received by the state machine while in the P-wave quarantine state, then a transition is made to a false P-wave state 116, indicative of a far field R-wave. The false P-wave state is also denoted herein as the "10/0" state or the "false atrial depolarization event state." Unlike the true P-wave state, the false P-wave state does not trigger forwarding of the P-wave interrupt to the microcontroller. Rather, the state machine simply remains within the false P-wave state until the timer expires, then transitions back to the idle state. Note that the false P-wave state is also reached if a P-wave interrupt and an R-wave interrupt are substantially simultaneously received by the state machine while in the idle state. Simultaneous receipt of a P-wave interrupt and an R-wave interrupt also activates the timer, eventually triggering the transition back to the idle state.

Table I below lists the various states of the state machine in terms of present state/next state and various excitation inputs, i.e. the interrupt and timer inputs. Within Table I, receipt of a P-wave from the sensing circuitry of FIG. 3 is denoted by P=1. Receipt of an R-wave from the sensing circuitry is denoted by R=1. Receipt of the time out event signal from the timer is denoted by FFT=1. The parameters y1 and y2 represent the present state. Y1 and Y2 represent the next state. Confirmation of a true P-wave is denoted as TrueP=1

TABLE I

Present State/Next State Table for the Far field Discriminator State Machine

| y1, y2, P, R, FFT | Y1 | Y2 | TrueP | Present State | Excitation Inputs | Next State |
|---|---|---|---|---|---|---|
| 00000 | 0 | 0 | 0 | Idle | None | Idle |
| 00001 | 0 | 0 | 0 | Idle | FFT = 1 | Idle (Fault) |
| 00010 | 0 | 0 | 0 | Idle | R = 1 | Idle |
| 00011 | 0 | 0 | 0 | Idle | R = 1, FFT = 1 | Idle (Fault) |
| 00100 | 0 | 1 | 0 | Idle | P = 1 | P-wave Quarantine |
| 00101 | 0 | 0 | 0 | Idle | P = 1, FFT = 1 | Idle (Fault) |
| 00110 | 1 | 0 | 0 | Idle | P = 1, R = 1 | False P-wave |
| 00111 | 0 | 0 | 0 | Idle | P = 1, R = 1, FFT = 1 | Idle (Fault) |
| 01000 | 0 | 1 | 0 | P-wave Quarantine | None | P-Wave Quarantine |
| 01001 | 1 | 1 | 1 | P-wave Quarantine | FFT = 1 | True P-wave |
| 01010 | 1 | 0 | 0 | P-wave Quarantine | R = 1 | False P-wave |
| 01011 | 1 | 0 | 0 | P-wave Quarantine | R = 1, FFT = 1 | False P-wave |
| 01100 | 0 | 1 | 0 | P-wave Quarantine | P = 1 | P-Wave Quarantine |
| 01101 | 1 | 1 | 1 | P-wave Quarantine | P = 1, FFT = 1 | True P-wave |
| 01110 | 1 | 0 | 0 | P-wave Quarantine | P = 1, R = 1 | False P-wave |
| 01111 | 1 | 0 | 0 | P-wave Quarantine | P = 1, R = 1, FFT = 1 | False P-wave |
| 10000 | 1 | 0 | 0 | False P-wave | None | False P-wave |
| 10001 | 0 | 0 | 0 | False P-wave | FFT = 1 | Idle |
| 10010 | 1 | 0 | 0 | False P-wave | R = 1 | False P-wave |
| 10011 | 0 | 0 | 0 | False P-wave | R = 1, FFT = 1 | Idle |
| 10100 | 1 | 0 | 0 | False P-wave | P = 1 | False P-wave |
| 10101 | 0 | 0 | 0 | False P-wave | P = 1, FFT = 1 | Idle |
| 10110 | 1 | 0 | 0 | False P-wave | P = 1, R = 1 | False P-wave |
| 10111 | 0 | 0 | 0 | False P-wave | P = 1, R = 1, FFT = 1 | Idle |
| 11000 | 0 | 0 | 0 | True P-wave | None | Idle |
| 11001 | 0 | 0 | 0 | True P-wave | FFT = 1 | Idle |
| 11010 | 0 | 0 | 0 | True P-wave | R = 1 | Idle |
| 11011 | 0 | 0 | 0 | True P-wave | R = 1, FFT = 1 | Idle |
| 11100 | 0 | 0 | 0 | True P-wave | P = 1 | Idle |
| 11101 | 0 | 0 | 0 | True P-wave | P = 1, FFT = 1 | Idle |
| 11110 | 0 | 0 | 0 | True P-wave | P = 1, R = 1 | Idle |
| 11111 | 0 | 0 | 0 | True P-wave | P = 1, R = 1, FFT = 1 | Idle |

Minimized functions relating the next state variables Y1 and Y2 to the present state variables y1 and y2 and the excitation inputs may be derived from the truth tables of FIG. 5 in accordance with otherwise conventional state machine logic techniques. The minimized functions are:

$$Y1 = y1'y2R + y1'y2FFT + y1PR FFT' + y1y2'FFT'$$

$$Y2 = y1'y2R' + y1'PR'FFT'.$$

Figure 6:
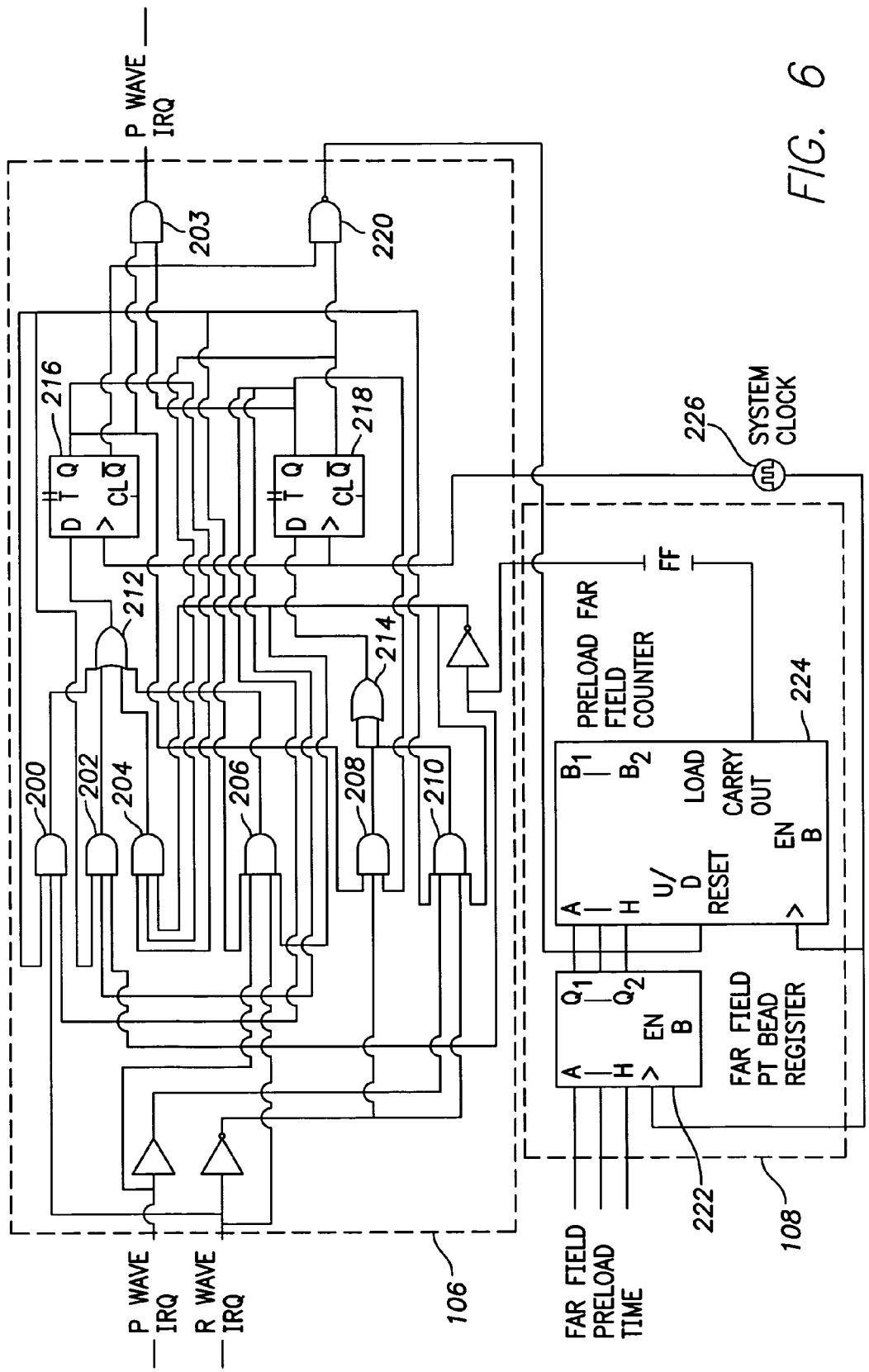
FIG. 6 is a circuit schematic illustrating state-machine circuitry of the quarantine circuit of FIG. 3.

FIG. 6 is a circuit schematic of one exemplary implementation of quarantine circuit 100 of FIG. 3. State machine 106 of FIG. 6 is implemented using AND gates 200-210, OR gates 212, 214, D flip flops 216, 218 and NAND gate 220, interconnected as shown. Timer 108 is implemented using a preload register 222 and preload counter 224, interconnected as shown. A system clock 226 of the pacer/ICD clocks D flip flops 216-218, register 222, and counter 224. Other specific circuits capable of representing the state machine of FIG. 4 may alternatively be used.

Figure 7:
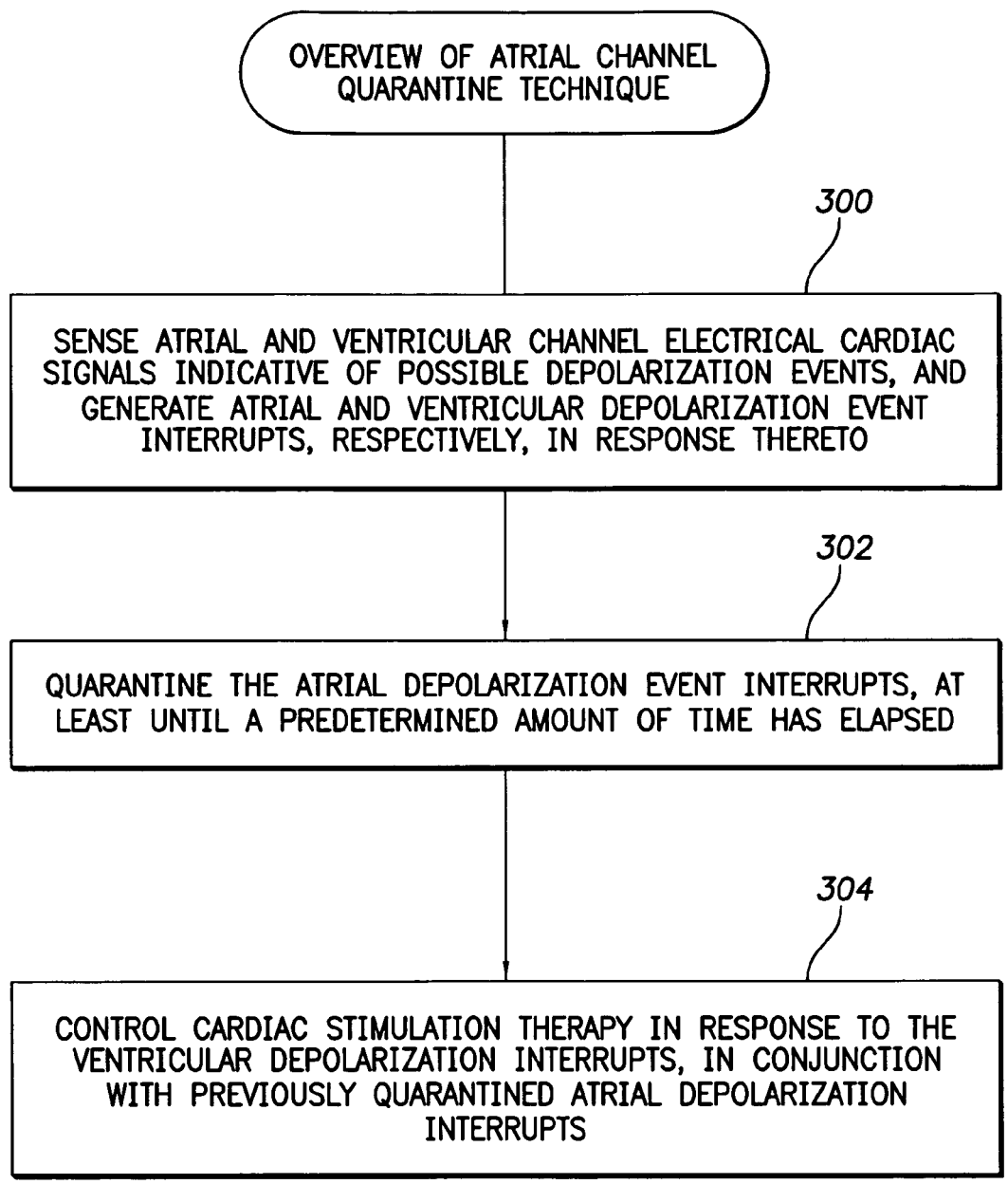
FIG. 7 is a flow chart summarizing, at a high level, steps performed using the components of FIG. 3.

FIG. 7 summarizes the techniques of the invention. Briefly, beginning at step 300, atrial and ventricular channel electrical cardiac signals indicative of possible depolarization events are sensed, and atrial and ventricular depolarization event interrupts, respectively, are generated in response thereto. At step 302, the atrial depolarization event interrupts are quarantined, at least until a predetermined amount of time has elapsed. Then, at step 304, cardiac stimulation therapy is controlled in response to the ventricular depolarization interrupts, in conjunction with previously quarantined atrial depolarization interrupts.

What have been described are techniques for discriminating near field P-waves from far field R-waves sensed in the atria. The techniques may be implemented in a wide range of implantable cardiac stimulation devices. For the sake of completeness, detailed descriptions of an exemplary pacer/ICD will now be described, in which the techniques are implemented.

Exemplary Pacer/ICD

Figure 8:
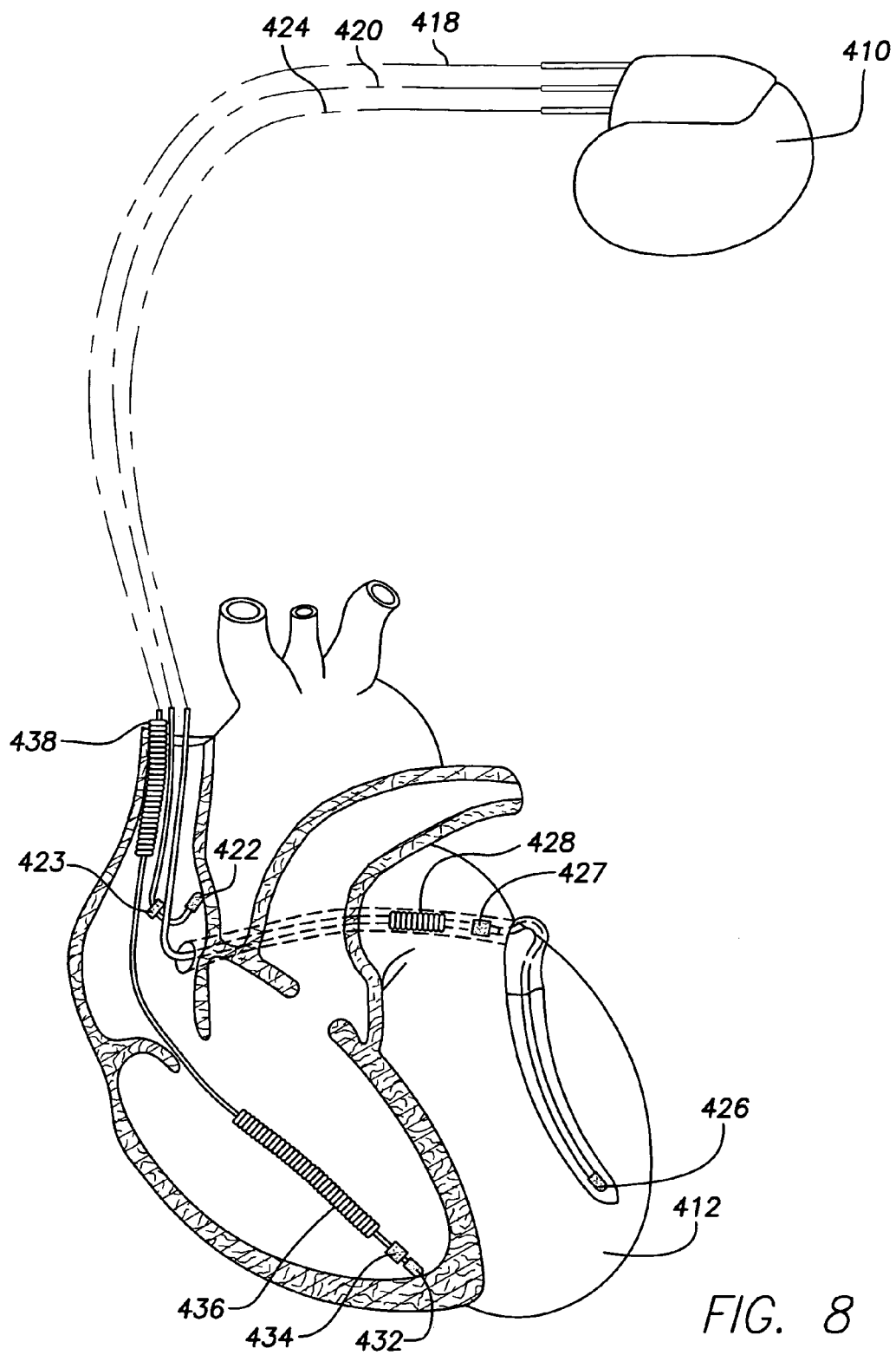
FIG. 8 is a simplified diagram illustrating an exemplary implementation of a pacer/ICD incorporating the quarantine circuit of FIG. 3.

FIG. 8 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 418 having, in this embodiment, a ventricular tip electrode 432, a right ventricular ring electrode 434, a right ventricular (RV) coil electrode 436, and a superior vena cava (SVC) coil electrode 438. Typically, the right ventricular lead 418 is transvenously inserted into the heart to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 9:
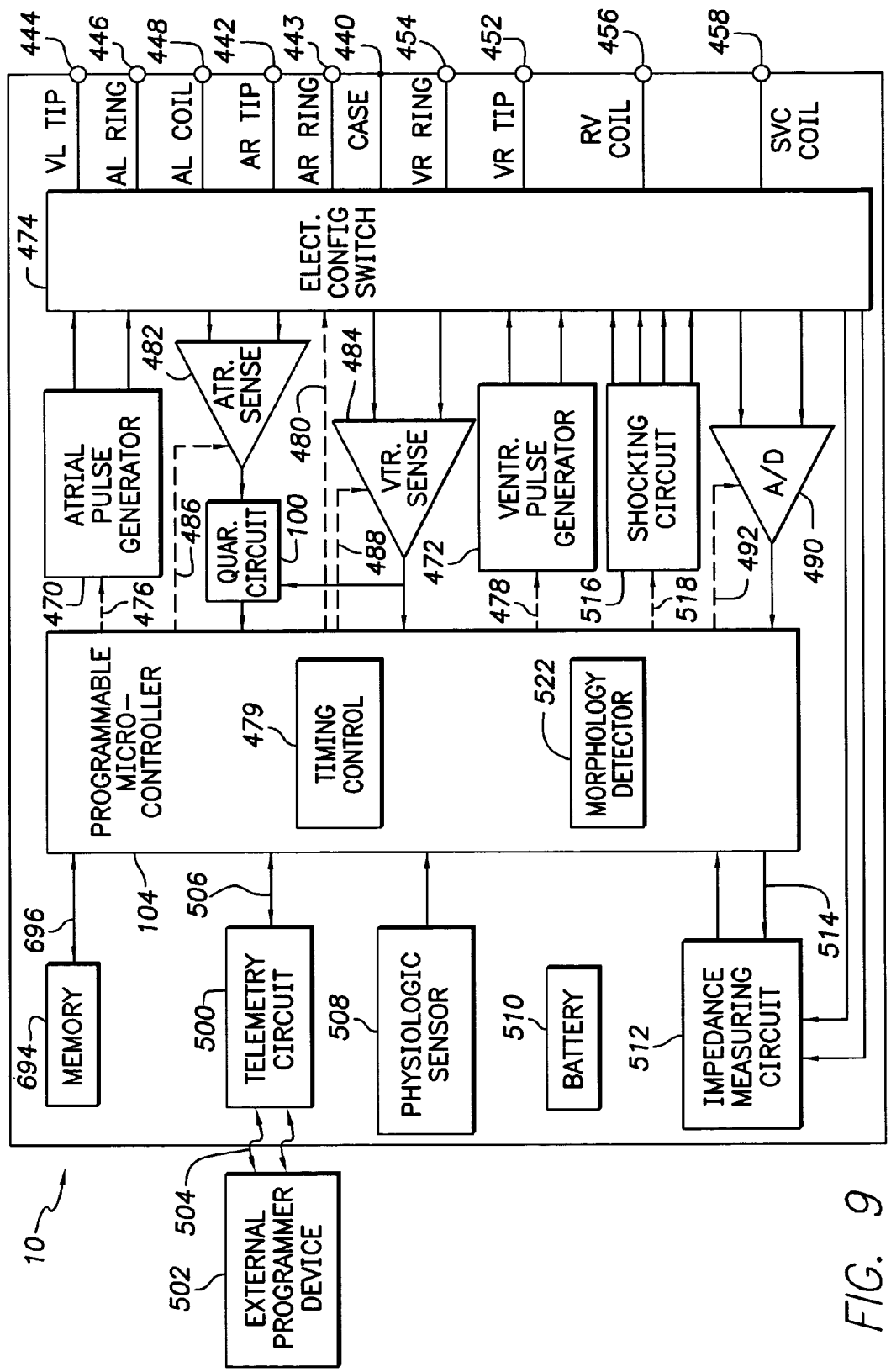
FIG. 9 is a functional block diagram illustrating internal components of the implantable device of FIG. 8.

A simplified block diagram of internal components of pacer/ICD 410 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 440 for pacer/ICD 410, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is microcontroller 104, which controls the various modes of stimulation therapy. As is well known in the art, the microcontroller 104 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 104 includes the ability to process or monitor input signals (data) as controlled by a program code stored in a designated block of memory. The details of the design and operation of the microcontroller 104 are not critical to the invention. Rather, any suitable microcontroller 104 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 418, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 104 via appropriate control signals, 476 and 478, respectively, to trigger or inhibit the stimulation pulses.

The microcontroller 104 further includes timing control circuitry (not separately shown) used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 104, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 418, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sense amplifiers may be in the form of interrupts. Collectively, switch 474 and sense amplifiers 482 and 484 correspond to sensing circuitry 102 of FIG. 3.

The outputs of the atrial and ventricular sensing circuits, 482 and 484, are connected to quarantine circuit 100, which, as explained above, forwards only those atrial channel interrupts to the microcontroller that correspond to true P-waves. The output of the ventricular sensing circuit 484 is also connected directly to the microcontroller for directly relaying ventricular event interrupts to the microcontroller.

The microcontroller 104 triggers or inhibits the atrial and ventricular pulse generators, 470 and 472, respectively, in a demand fashion in response to the absence or presence of cardiac activity in the appropriate chambers of the heart, as represented by the atrial and ventricular event interrupts.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 104 by comparing them to a predefined rate zone limit (i.e., bradycardia, normal, atrial tachycardia, atrial fibrillation, low rate ventricular tachycardia, high rate ventricular tachycardia, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 418 through the switch 474 to sample cardiac signals across any pair of desired electrodes. The microcontroller 104 is further coupled to a memory 494 by a suitable data/address bus 496, wherein the programmable operating parameters used by the microcontroller 104 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 104 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 104 responds by adjusting the various pacing parameters (such as rate, atrioventricular delay (AV), V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 9. The battery 510 may vary depending on the capabilities of pacer/ICD 410. If the system only provides low-voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, pacer/ICD 410 is preferably capable of high-voltage therapy and appropriate batteries.

As further shown in FIG. 9, pacer/ICD 410 is shown as having an impedance measuring circuit 512 which is enabled by the microcontroller 104 via a control signal 514. The circuit measures impedance values for use by components of the microcontroller for performing subsequent estimates of defibrillation impedance in accordance with the techniques above. Impedance values may also be used for tracking respiration; for surveillance during the acute and chronic phases for proper lead positioning or dislodgement; for measuring respiration or minute ventilation; for measuring thoracic impedance for use in setting shock thresholds; for detecting when the device has been implanted; and for detecting the opening of heart valves, etc. The impedance measuring circuit 120 is advantageously coupled to the switch 74 so that any desired combination of electrodes may be used.

In the case where pacer/ICD 410 is intended to operate as an ICD, it detects the occurrence of an arrhythmia, and automatically applies an appropriate electrical shock therapy to the heart aimed at terminating the detected arrhythmia. To this end, the microcontroller 104 further controls a shocking circuit 516 by way of a control signal 518. The shocking circuit 516 generates shocking pulses of low (up to 0.5 joules), moderate (0.5-10 joules) or high energy (11 to 40 joules or more), as controlled by the microcontroller 104. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with a VS event and/or pertaining to the treatment of tachycardia. Defibrillation shocks are generally of moderate to high energy level (i.e., corresponding to thresholds in the range of 5-40 joules), delivered asynchronously (since VS events may be too disorganized), and pertaining exclusively to the treatment of fibrillation. Accordingly, the microcontroller 104 is capable of controlling the synchronous or asynchronous delivery of the shocking pulses.

In addition, the stimulation device may be configured to perform AMS wherein the pacemaker automatically reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Thus, various techniques have been set forth for discriminating near field atrial events from far field ventricular events within an atrial sensing channel. Although described primarily with respect to the filtering of far field ventricular events from signals sensed in the atrial, aspects of the invention could potentially also be exploited to filter far field atrial events from near field ventricular signals. As can be appreciated, a wide variety of embodiments can be implemented consistent with the principles the invention and no attempt is made herein to describe all possible techniques. Moreover, although described primarily with reference to an example wherein the implanted device is a defibrillation/pacer, principles of the invention are applicable to other implantable cardiac stimulation devices as well such as pacemakers without defibrillation capability. The various functional components of the exemplary systems may be implemented using any appropriate technology, including application specific integrated circuits (ASICs) executing hard-wired logic operations.

In general, the exemplary embodiments of the invention described herein are merely illustrative of the invention and should not be construed as limiting the scope of the invention. Note also that the term "including" as used herein is intended to be inclusive, i.e. "including but not limited to."

What is claimed is:

1. A system for use in an implantable cardiac stimulation device, said system comprising:
   sensing circuitry operative to sense electrical cardiac signals indicative of possible first-chamber cardiac depolarization events and possible second-chamber cardiac depolarization events, to generate corresponding first-chamber event interrupts and second chamber event interrupts in response thereto, and to output second chamber event interrupts without delay, the sensing circuit comprising atrial channel sensing circuitry for sensing atrial channel signals indicative of possible atrial depolarization events corresponding to first-chamber cardiac depolarizations and generating atrial depolarization event interrupts corresponding to first-chamber event interrupts in response thereto; and ventricular channel sensing circuitry for sensing ventricular channel signals indicative of possible ventricular depolarization events corresponding to second-chamber cardiac depolarizations and generating ventricular depolarization event interrupts corresponding to second-chamber event interrupts in response thereto;
   a microcontroller operative to control cardiac stimulation therapy in response to the interrupts; and
   a quarantine circuit interposed between the sensing circuitry and the microcontroller and operative to delay receipt of a first-chamber event interrupt by the microprocessor for at least a predetermined time period and to prevent receipt of the first-chamber event interrupt by the microprocessor if a second-chamber event interrupt is generated during the time period, the quarantine circuit comprising a timer for timing the predetermined time period; and a hardware state machine operative, in response to receipt of an atrial depolarization event interrupt, to forward the atrial interrupt to the microcontroller after the timer expires so long as no ventricular depolarization event interrupt is received before the timer expires;
   wherein the microcontroller is further operative to process the first-chamber event interrupt and the second-chamber event interrupt, taking into account the predetermined time period, to determine a cardiac signal interval and the state machine is operative to selectively transition among an idle state, a quarantine state, a true atrial depolarization event state, and a false atrial depolarization event state.

2. The system of claim 1 wherein receipt of an atrial depolarization event interrupt while in the idle state, without receipt of a substantially simultaneous ventricular depolarization event interrupt, triggers a transition from the idle state to the quarantine state.

3. The system of claim 1 wherein expiration of the timer while in the quarantine state, without receipt of a ventricular depolarization event interrupt prior to expiration of the timer, triggers a transition to the true atrial depolarization event state.

4. The system of claim 3 wherein transition to the true atrial depolarization event state triggers output of the atrial depolarization event interrupt to the microcontroller.

5. The system of claim 1 wherein receipt of a ventricular depolarization event interrupt while in the quarantine state triggers a transition to the false atrial depolarization event state.

6. The system of claim 1 wherein expiration of the timer while in the false atrial depolarization event state triggers a transition to the idle state.

7. The system of claim 1 wherein expiration of the timer while in the true atrial depolarization event state triggers a transition to the idle state.

8. The system of claim 1 wherein substantially simultaneous receipt of an atrial depolarization event interrupt and a ventricular depolarization event interrupt while in the idle state triggers a transition to the false atrial depolarization event state.

9. The system of claim 1 wherein the microcontroller is operative to control cardiac stimulation therapy by analyzing sequences of the interrupts, then delivering therapy in response thereto.

10. A system for use in an implantable cardiac stimulation device, said system comprising:
    sensing circuitry operative to sense electrical cardiac signals indicative of possible first-chamber cardiac depolarization events and possible second-chamber cardiac depolarization events, to generate corresponding first-chamber event interrupts and second chamber event interrupts in response thereto, and to output second chamber event interrupts without delay, the sensing circuit comprising atrial channel sensing circuitry for sensing atrial channel signals indicative of possible atrial depolarization events corresponding to first-chamber cardiac depolarizations and generating atrial depolarization event interrupts corresponding to first-chamber event interrupts in response thereto; and ventricular channel sensing circuitry for sensing ventricular channel signals indicative of possible ventricular depolarization events corresponding to second-chamber cardiac depolarizations and generating ventricular depolarization event interrupts corresponding to second-chamber event interrupts in response thereto;
    a microcontroller operative to control cardiac stimulation therapy in response to the interrupts; and a quarantine circuit interposed between the sensing circuitry and the microcontroller and operative to delay receipt of a first-chamber event interrupt by the microprocessor for at least a predetermined time period and to prevent receipt of the first-chamber event interrupt by the microprocessor if a second-chamber event interrupt is generated during the time period, the quarantine circuit comprising a timer for timing the predetermined time period; and a hardware state machine operative, in response to receipt of an atrial depolarization event interrupt, to forward the atrial interrupt to the microcontroller after the timer expires so long as no ventricular depolarization event interrupt is received before the timer expires;

wherein the microcontroller is further operative to process the first-chamber event interrupt and the second-chamber event interrupt, taking into account the predetermined time period, to determine a cardiac signal interval and the state machine is implemented as a Moore-type circuit with D-flip flops wherein the timer is implemented as a pre-loadable counter/register.

* * * * *